(12) United States Patent
Iwanaga et al.

(10) Patent No.: US 9,204,793 B2
(45) Date of Patent: Dec. 8, 2015

(54) OPHTHALMOLOGIC APPARATUS AND OPHTHALMOLOGIC PHOTOGRAPHING METHOD

(75) Inventors: Tomoyuki Iwanaga, Yokohama (JP); Hiroshi Aoki, Saitama (JP); Hirofumi Yoshida, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 247 days.

(21) Appl. No.: 13/595,221

(22) Filed: Aug. 27, 2012

(65) Prior Publication Data
US 2013/0100407 A1    Apr. 25, 2013

(30) Foreign Application Priority Data
Oct. 19, 2011    (JP) .................. 2011-230026

(51) Int. Cl.
| A61B 3/14 | (2006.01) |
| A61B 3/15 | (2006.01) |
| A61B 3/10 | (2006.01) |
| A61B 3/12 | (2006.01) |

(52) U.S. Cl.
CPC .............. *A61B 3/152* (2013.01); *A61B 3/102* (2013.01); *A61B 3/1225* (2013.01)

(58) Field of Classification Search
USPC .............. 351/200, 205–209, 211, 221–223
See application file for complete search history.

(56) References Cited

U.S. PATENT DOCUMENTS

| 5,751,396 A * | 5/1998 | Masuda et al. ............... 351/221 |
| 2003/0076477 A1* | 4/2003 | Matsumoto .................. 351/206 |
| 2007/0002277 A1* | 1/2007 | Hanebuchi .................... 351/206 |
| 2009/0323023 A1* | 12/2009 | Kogawa et al. ............... 351/208 |

FOREIGN PATENT DOCUMENTS

| JP | 61-185246 A | 8/1986 |
| JP | 63-229629 A | 9/1988 |
| JP | H09-066027 A | 3/1997 |
| JP | 10-192244 A | 7/1998 |
| JP | 2001-327471 A | 11/2001 |
| JP | 2007-275160 A | 10/2007 |
| JP | 2009-160190 A | 7/2009 |
| JP | 2010-142428 A | 7/2010 |
| JP | 2010-162424 A | 7/2010 |
| JP | 2011-147609 A | 8/2011 |

* cited by examiner

*Primary Examiner* — Joseph P Martinez
*Assistant Examiner* — Brandi Thomas
(74) *Attorney, Agent, or Firm* — Canon U.S.A., Inc., IP Division

(57) ABSTRACT

An ophthalmologic apparatus including a splitting unit configured to split, on a light path in an optical observation system of an anterior segment of a subject's eye, an anterior segment image into a plurality of light beams at a position conjugated with the anterior segment, and an imaging unit configured to capture the anterior segment image via an image forming unit configured to form an image of the light beams coming from the anterior segment, split by the splitting unit.

13 Claims, 5 Drawing Sheets

OPHTHALMOLOGIC APPARATUS AND OPHTHALMOLOGIC PHOTOGRAPHING METHOD

BACKGROUND OF THE INVENTION

1. Field of the Invention

The present invention relates to alignment of an ophthalmologic apparatus, and more specifically to alignment using an anterior segment image.

2. Description of the Related Art

Currently, an optical tomographic imaging apparatus based on optical coherence tomography (hereinafter referred to as "OCT") that uses multi wavelength interference can obtain a tomographic image of a sample at a high resolution. Such an optical tomographic imaging apparatus is becoming indispensible in retina clinics as an ophthalmology instrument.

With the above-described OCT apparatus, measurement light, which is low-coherence light, is radiated onto a sample, and the backscattered light from that sample can be measured at a high resolution using an interference system or an interference optical system. Further, a high resolution tomographic image can be obtained by the OCT apparatus scanning the sample with this measurement light. Consequently, a tomographic image of the retina at the fundus of a subject's eye is acquired, which is widely used in the ophthalmologic diagnosis of the retina.

On the other hand, generally, in an ophthalmologic apparatus it is important that the examination unit (mainly the optical measurement system) in the apparatus for capturing an image is accurately aligned with the subject's eye to be examined, and that the fundus tomographic image is correctly focused.

Japanese Patent Application Laid-Open No. 2010-162424 discusses an ophthalmologic apparatus that projects an alignment mark on the cornea of a subject's eye, captures an image with an image sensor by splitting the reflected light from the cornea, detects the relative position between the apparatus and the subject's eye based on the position of the split alignment mark image, and aligns the positions of the apparatus and the subject's eye.

Further, Japanese Patent Application Laid-Open No. 2001-327471 discusses a fundus detection apparatus that detects the relative position between the apparatus and a subject's eye in a plane perpendicular to the optical axis and aligns their positions by capturing an image of the anterior segment of a subject's eye, determining an intersection between two scanning lines and a pupil edge on the image, and calculating the deviation, i.e., the misalignment, between these light paths and the pupil.

In addition, in Japanese Patent Application Laid-Open No. 10-192244, an image splitter for splitting an anterior segment image of a subject's eye is arranged in an optical system for anterior segment observation. The optical system is detachably arranged between a perforated mirror and an objective lens. The perforated mirror splits the light into an illumination light path and an observation imaging light path. The operator aligns the apparatus and the subject's eye by observing the image-split anterior segment image displayed on a monitor. When capturing an image of the fundus, alignment is performed while observing a separately-provided alignment mark image, which is not in the light path. When the subject's eye and the apparatus reach a predetermined position, the image is captured.

In Japanese Patent Application Laid-Open No. 2010-162424, a unit for projecting the alignment mark onto the cornea of the subject's eye is necessary. Further, it is not uncommon for the pupil in a subject's eye to be off center with respect to the cornea, so that if alignment is performed based on the alignment mark image projected onto the cornea, the subject's eye pupil does not match the optical axis of the apparatus. This can cause the measurement light beams to be shaded by the pupil if the pupil diameter of the subject's eye is small.

Further, in Japanese Patent Application Laid-Open No. 2001-327471, although misalignment of the subject's eye pupil in the plane perpendicular to the optical axis of the apparatus can be detected, the distance between the apparatus and the subject's eye in the optical axis direction, i.e., the operational distance, cannot be detected. Consequently, a unit for detecting the operational distance has to be separately provided.

Moreover, in Japanese Patent Application Laid-Open No. 10-192244, since the anterior segment of the subject's eye cannot be observed when capturing an image of the fundus, image capturing has to be performed while confirming that unnecessary reflected light from the subject's eye has not entered into a circumferential portion of the observed fundus image. Consequently, an experienced operator is required.

Further, when observing the fundus, it is commonly known to project an alignment mark onto the cornea of the subject's eye and perform alignment while observing this mark along with the fundus image. However, even in such an apparatus, how much the imaging optical axis deviates from the subject's eye pupil when capturing an image of the fundus cannot be confirmed.

In addition, when projecting an alignment mark onto the cornea of the subject's eye and detecting the reflected light from the cornea, if the positional relationship between the apparatus and the subject's eye substantially deviates, the reflected light from the cornea cannot be detected.

SUMMARY OF THE INVENTION

The present invention is directed to providing an ophthalmologic apparatus that performs alignment using an anterior segment image.

According to an aspect of the present invention, an ophthalmologic apparatus includes a splitting unit configured to split, on a light path in an optical observation system of an anterior segment of a subject's eye, an anterior segment image into a plurality of light beams at a plane conjugated with the anterior segment, and an imaging unit configured to capture the anterior segment image via an image forming unit configured to form an image of the light beams coming from the anterior segment, split by the splitting unit.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

A first exemplary embodiment according to the present invention will now be described. In the first exemplary embodiment, an example will be described using FIG. 1 in which the present invention is applied to an optical tomographic imaging apparatus (OCT) as an example of an ophthalmologic apparatus.

(General Configuration of the Apparatus)

Figure 1:
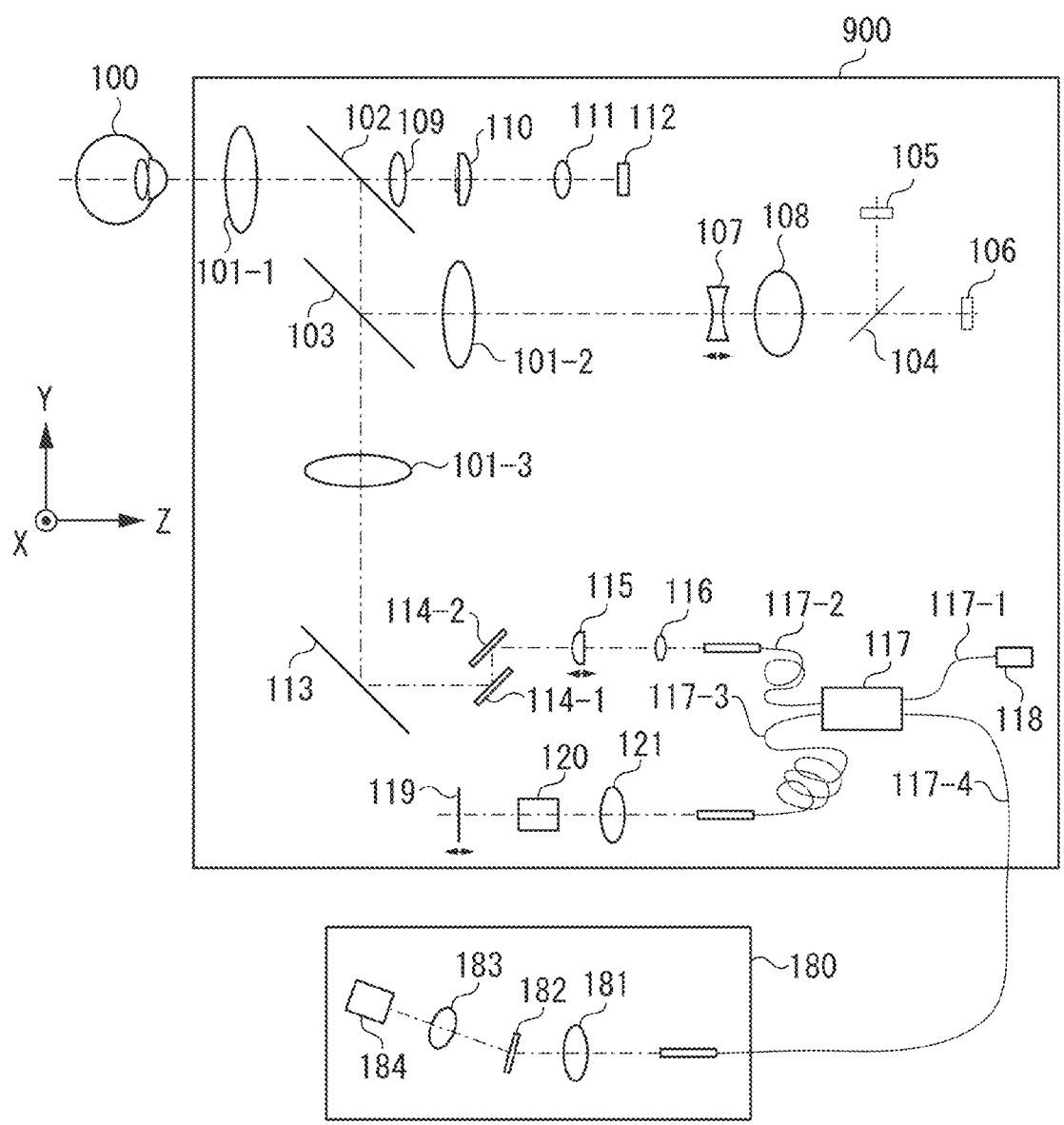
FIG. 1 illustrates acquisition of a tomographic image by an OCT apparatus according to a first exemplary embodiment of the present invention.

The general configuration of the ophthalmologic apparatus according to the present exemplary embodiment will be described with reference to FIG. 1. FIG. 1 is a side view of an ophthalmologic apparatus that includes an optical head 900. The optical head 900 is an optical measurement system for capturing an anterior eye image, a two-dimensional of the fundus, and a tomographic image. The drive controls described below are controlled by a control unit 1000 acting as a control means having a (not illustrated) central processing unit (CPU).

(Configuration of Optical Measurement System and Spectroscope)

The configuration of the optical measurement system and the spectroscope according to the present exemplary embodiment will be described with reference to FIG. 1. First, the internal configuration of the optical head 900 will be described. An objective lens 101-8 is arranged facing a subject's eye 100, and on that optical axis, a first dichroic mirror 102 as a first light path splitting unit and a second dichroic mirror 103 as a second light path splitting unit are arranged.

Light is split by the first dichroic mirror 102 and the second dichroic mirror 103 into a light path L1, a light path L2, and light Path L3 for respective wavelength bands. The light path L1 is a measurement light path for an optical system in a light interference tomographic imaging unit. The light path L2 is a light path for fundus observation and for a fixation lamp. The light path L3 is a light path for an optical observation system of an anterior eye.

The light path L2 is also split into light paths for different wavelength bands by a third dichroic mirror 104. The third dichroic mirror 104 acts as a third light splitting unit into a light path to a charged-couple device (CCD) 105 for fundus observation and to a fixation lamp 106. The optical head 900 includes lenses 101-2, 107, and 108. The lens 107 is driven by a (not illustrated) motor based on a command from the control unit 1000 for focus adjustment of the fixation lamp and fundus observation. The CCD 105 is sensitive to the wavelength of (not illustrated) illumination light for fundus observation, specifically, around 780 nm. On the other hand, the fixation lamp 106 generates visible light to help the visual fixation of the subject.

On the light path L3, a lens 109 and a prismatic lens 110 acting as a splitting unit are arranged. The prismatic lens 110 has an image splitting prism for splitting the light from the anterior segment image into a plurality of light beams at a position conjugated with the anterior segment of the subject's eye 100. This prismatic lens 110 has an image splitting prism function on a first face seen from the subject side, and a lens function on a second face. A lens 111 acts as a relay optical system for relaying an optical image. An infrared ray CCD 112 for anterior eye observation captures an image of the anterior segment image formed by the lens 111, which acts as an image forming unit. The CCD 112 acting as an imaging unit is sensitive to the wavelength of (not illustrated) illumination light for anterior segment observation, specifically, around 970 nm.

As stated above, the light path L1 forms an OCT optical system for capturing a tomographic image of the fundus of a subject's eye 100. More specifically, the light path L1 is provided to obtain an interference signal for forming a tomographic image. On the light path L1 are arranged a lens 101-3, a mirror 113, an X-scanner 114-1 and a Y-scanner 114-2 for scanning the fundus of the subject's eye 100, and lenses 115 and 116. The lens 115 is driven by a (not illustrated) motor to adjust the focus on the subject's eye 100 of light from a light source 118. The light source 118 radiates light coming from a fiber 117-2 which is connected to an optical coupler 117. Based on this focus adjustment, the light from the subject's eye 100 is simultaneously incident on a tip of the fiber 117-2 to form a spot-like image.

Next, the light path from the light source 118 and the configuration of a reference optical system and a spectroscope will be described. The optical head 900 includes the light source 118, a mirror 119, glass 120 for scattered light compensation, the above-described optical coupler 117, single-mode optical fibers 117-1 to 117-4 that are integrally connected to the optical coupler, a lens 121, and a spectroscope 180.

A Michelson interference system is configured by this configuration. The light radiated from the light source 118 passes through the optical coupler 117 via the optical fiber 117-1, and is split into measurement light on the optical fiber 117-2 side and reference light on the optical fiber 117-3 side. The measurement light passes through the above-described OCT optical system, is radiated onto the fundus of the subject's eye 100, which is the observation target, and reaches the optical coupler 117 via the same light path, owing to reflection and scattering caused by retina.

On the other hand, the reference light reaches and is reflected by the mirror 119 via the glass 120 for scattered light compensation, which is inserted to match the scattering of the reference light with the measurement light. The reference light returns along the same light path, and reaches the optical coupler 117. At the optical coupler 117, the measurement light and the reference light merge to form interference light. This interference is produced when the light wavelength of the measurement light and the light wavelength of the reference light are nearly the same. The mirror 119 is adjustably held in the optical axis direction based on a command from the control unit 1000 by a (not illustrated) motor and a drive mechanism, so that the light wavelength of the reference light can be made to match the light wavelength of the measurement light that changes based on the subject's eye 100. The interference light is guided to the spectroscope 180 via the optical fiber 117-4.

The spectroscope 180 is configured from lenses 181 and 183, a diffraction grating 182, and a line sensor 184. The interference light radiated from the optical fiber 117-4 passes through the lens 181. After that, the interference light becomes roughly parallel, is then split by the diffraction grating 182, and is formed into an image on the line sensor 184 by the lens 183.

Next, the vicinity of the light source 118 will be described. The light source 118 is a super luminescent diode (SLD), which is a representative low-coherence light source. The center wavelength is 855 nm, and the wavelength band width is about 100 nm. Since the band width has an influence on the resolution in the optical axis direction of the obtained tomographic image, it is an important parameter. Further, although in this example an SLD is selected as the type of light source, as long as low-coherence light can be emitted, some other light source may be used, such as amplified spontaneous emission (ASE). Considering that the center wavelength measures the eye, near infrared light is suitable for measurement. Further, since the center wavelength has an influence on the resolution in the sideways direction of the obtained tomographic image, it is desirable for this wavelength to be as short as possible. For both of these reasons, a center wavelength of 855 nm is selected.

In the present exemplary embodiment, although a Michelson interferometer is used as an interferometer, a Mach-Zehnder interferometer may also be used. Depending on the difference in the quantity of light between the measurement light and the reference light, it is desirable to use a Mach-Zehnder interferometer when the difference in the quantity of light is large and a Michelson interference when the difference in the quantity of light is comparatively small.

(Method for Capturing Tomographic Image)

A method for capturing a tomographic image using an optical tomographic imaging apparatus will now be described. The optical tomographic imaging apparatus can capture a tomographic image of a desired site on the fundus of the subject's eye 100 by controlling the X-scanner 114-1 and the Y-scanner 114-2.

Figure 2:
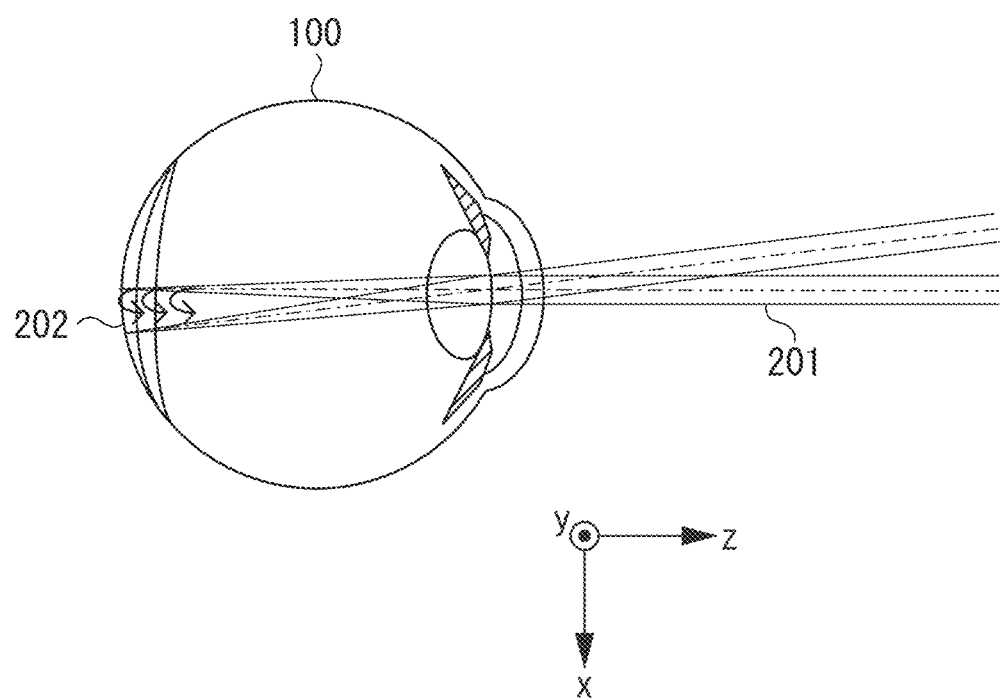
FIG. 2 illustrates scanning of a subject's eye in an x direction.

FIG. 2 illustrates scanning of a fundus 202 in the x direction by radiating measurement light 201 on the subject's eye 100. Information about a predetermined number of images from an imaging region in the x direction of the fundus 202 is captured by the line sensor 184. A luminance distribution on the line sensor 184 obtained at a predetermined position in the x direction will be referred to as FFT. The data obtained by converting a linear luminance distribution based on the FFT into density or color information will be referred to as an A scan image. A two-dimensional image formed by arranging a plurality of these A scan images will be referred to as a B scan image. After capturing the plurality of A scan images required to form one B scan image, the scan position is moved in the y direction and again scanning is carried out in the x direction to obtain a plurality of B scan images.

The plurality of B scan images, or a three-dimensional tomographic image formed from a plurality of B scan images, can be used by the operator for diagnosis of the subject's eye by displaying the image(s) on a monitor.

Figure 3:
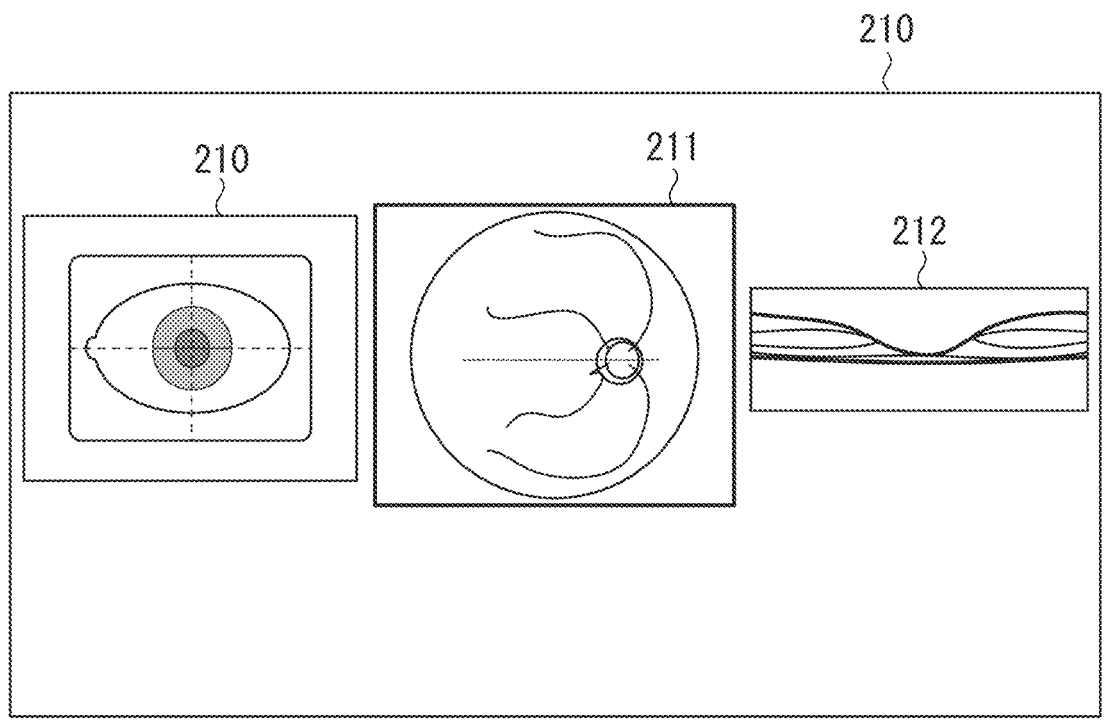
FIG. 3 illustrates an anterior eye image, a fundus two-dimensional image, and a B scan image displayed on a monitor.

FIG. 3 illustrates an anterior eye image 210, a fundus two-dimensional image 211, and a B scan image 212, which is a tomographic image, displayed on a monitor 200. The anterior eye image 210 is obtained by processing an output from the CCD 112, the fundus two-dimensional image 211 is obtained by processing an output from the CCD 105, and the B scan image 212 is formed by performing the above-described processing based on outputs from the line sensor 184.

(Method for Detecting Alignment Based on an Anterior Eye Image)

Figure 4:
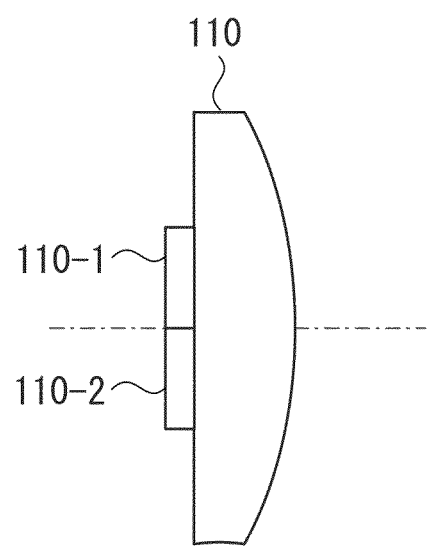
FIG. 4 illustrates a prismatic lens having an image splitting prism.

FIG. 4 illustrates in detail a prismatic lens 110 having an image splitting prism that splits the light beams at a position conjugated with the anterior segment of the subject's eye 100. In the prismatic lens 110, Fresnel prisms 110-1 and 110-2 are arranged at a position conjugated with the anterior segment of the subject's eye 100. Further, the opposite face of the Fresnel prisms 110-1 and 110-2 is spherical, so that the prismatic lens 110 acts as a field lens with respect to the anterior segment of the subject's eye 100. Consequently, the size of the lens 111 arranged at the back side can be reduced.

Figure 5A:
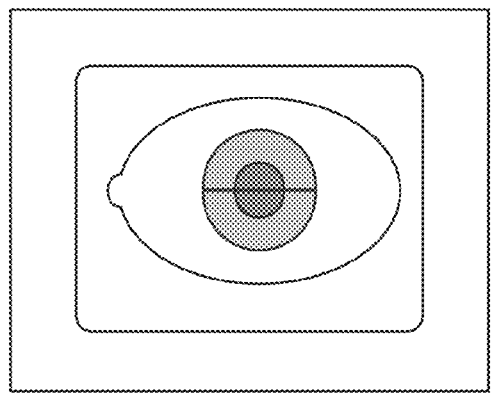
FIGS. 5A to 5D illustrate an anterior segment image captured on a CCD.

If the positional relationship between this optical tomographic imaging apparatus and the subject's eye 100, i.e., the alignment position, is ideal, the light beams from the anterior segment of the subject's eye 100 form an image on the Fresnel prisms 110-1 and 110-2 of the prismatic lens 110. Then, the formed image is split due to the effects of the prisms. Because the imaging face of the CCD 112 is also conjugated with the Fresnel prisms 110-1 and 110-2, an anterior eye image like that illustrated in FIG. 5A is formed by the CCD 112.

Figure 5B:
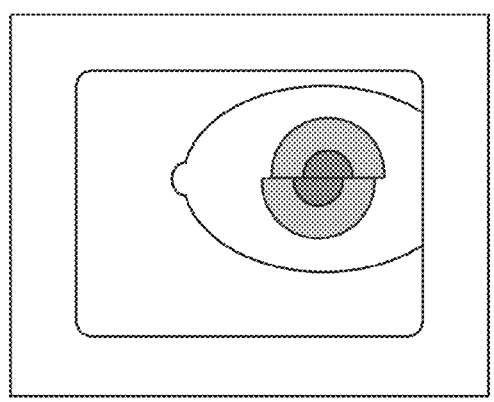
Figure 5C:
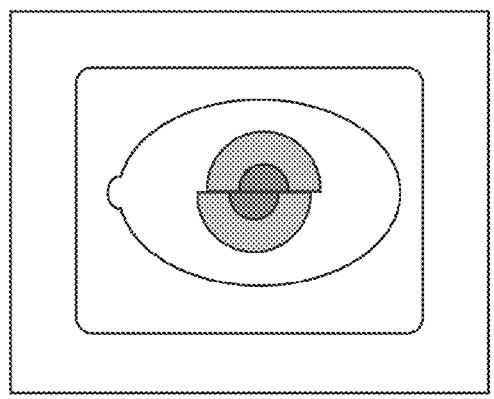
Figure 5D:
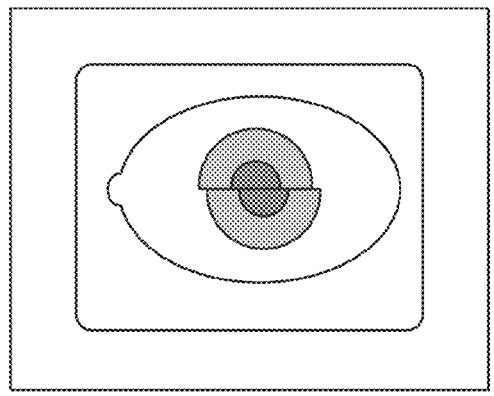

If the alignment position is not ideal in each of the X, Y, and Z directions, an anterior eye image like that illustrated in FIG. 5B is formed. Further, if the alignment position is ideal in the X and Y directions, but too far in the Z direction, an anterior eye image like that illustrated in FIG. 5C is formed. If the alignment position is ideal in the X and Y directions, but too close in the Z direction, an anterior segment image like that illustrated in FIG. 5D is formed.

Thus, the prismatic lens 110 is arranged at a position that is approximately conjugated with the anterior segment of the subject's eye 100 on the light path L3 for anterior eye observation, and the pupil position in the subject's eye 100 is detected by the image processing unit 2000 acting as a (not illustrated) image processing means based on the anterior eye image captured by the CCD 112. As a consequence, the alignment positional relationship between the optical tomographic imaging apparatus and the subject's eye 100 can be detected.

The image processing unit 2000 extracts a pupil region from an image of the anterior segment, and quantifies the position of the center of gravity in the pupil image as a position on the imaging face of the CCD 112. The control unit 1000 drives the optical head 900 based on an output from the image processing unit 2000 in left/right directions with a (not illustrated) XYZ stage so that the center of gravity in the pupil image is positioned in the center of the imaging face of the CCD 112.

Further, the image processing unit 2000 quantifies the split state of the pupil image by extracting the pupil region from the image of the anterior segment. This method is performed by the image processing unit 2000 binarizing the captured anterior segment image and extracting from the binarized image a linear component as the position where the image structure is split. Further, the image processing unit 2000 extracts edge positions of the split pupil image which are equal distances from the linear component.

The image processing unit 2000 quantifies the level of misalignment of the edge positions of the pupil image, and outputs the obtained data to the control unit 1000.

The control unit 1000 controls the position of the optical head 900 forwards or backwards based on a state in which the anterior segment image has been split. Specifically, the control unit 1000 drives and controls a motor in a (not illustrated) drive unit in the forwards/backwards directions to position the optical head 900 in a (not illustrated) XYZ stage to place the pupil of the subject's eye 100 at the ideal position based on the output from the image processing unit 2000. Further, the anterior segment of the subject's eye 100 can be constantly monitored even while capturing the tomographic image.

While an OCT was described in the present exemplary embodiment, the OCT can also be applied to a fundus camera by replacing the light path L1 with a fundus camera optical system as a fundus imaging unit that captures the returning light from the fundus of a subject's eye. Further, similarly, the skilled person would find it easy to install the OCT in an ophthalmologic apparatus such as a tonometer, a corneal shape measurement apparatus, a vision analyzer.

As described above, in the optical tomographic imaging apparatus according to the present exemplary embodiment, an alignment mark is not necessary, the positional relationship between the pupil in a subject's eye and the apparatus is constantly known, and shading of the measurement light due to the pupil is reduced even for a subject's eye that has a small pupil. Consequently, deterioration in the quality of the obtained OCT is reduced. Further, since it is not necessary to detect reflected light from the cornea in the subject's eye, an OCT image can be provided with a wide detection region as to the relative position between the apparatus and the pupil in the subject's eye.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2011-230026 filed Oct. 19, 2011, which is hereby incorporated by reference herein in its entirety.

What is claimed is:

1. An ophthalmic apparatus comprising:
    an optical observation system configured to observe an anterior segment of a subject's eye;
    an imaging system configured to capture an image of a fundus of the subject's eye; and
    a light path splitting unit configured to split a light path in the optical observation system and a light path in the imaging system;
    wherein the optical observation system comprises;
        an image splitting unit configured to split, on the light path in the optical observation system split by the light path splitting unit, a light beam reflected from the anterior segment into a plurality of light beams at a position conjugated with the anterior segment; and
        an anterior segment imaging unit configured to capture the plurality of light beams split by the image splitting unit to form an image of the anterior segment, and
    wherein the imaging system comprises;
        an irradiation unit configured to irradiate the fundus of the subject's eye with a measurement light; and
        a fundus imaging unit configured to capture a reflected light of the measurement light reflected from the fundus to form the image of the fundus.

2. The ophthalmic apparatus according to claim 1, wherein the image splitting unit has an image splitting prism function on a first face and a lens function on a second face.

3. The ophthalmic apparatus according to claim 1, wherein the optical observation system further comprises a relay optical system configured to relay the plurality of light beams split by the image splitting unit, and wherein the plurality of light beams relayed by the relay optical system is captured by the anterior segment imaging unit.

4. The ophthalmic apparatus according to claim 1, further comprising a control unit configured to control a position of the optical observation system relative to the anterior segment in at least one of a forwards/backwards direction and a left/right direction.

5. The ophthalmic apparatus according to claim 4, wherein the control unit is configured to control in a forwards/backwards direction a position of the observation optical system based on a state in which the anterior segment image is split.

6. The ophthalmic apparatus according to claim 4, wherein the control unit is configured to control in a left/right direction a position of the optical observation system based on a position of the anterior segment image relative to the anterior segment imaging unit.

7. The ophthalmic apparatus according to claim 4, further comprising an image processing unit configured to process the image of the anterior segment captured by the anterior segment image unit,
    wherein the control unit is configured to control a position of the optical observation system relative to the anterior segment based on an output from the image processing unit.

8. The ophthalmic apparatus according to claim 7, wherein the image processing unit is configured to extract a pupil region from the anterior segment image and quantify a split state of a pupil image of the pupil region.

9. The ophthalmic apparatus according to claim 7, wherein the image processing unit is configured to extract a pupil region from the anterior segment image and quantify a gravity center position of a pupil image of the pupil region.

10. The ophthalmic apparatus according to claim 4, wherein the control unit is configured to control a drive unit that drives an optical head that includes the observation optical system and the imaging system.

11. The ophthalmic apparatus according to claim 1, further comprising:
    a fundus observation system configured to observe the fundus of the subject's eye; and
    a second light path splitting unit configured to split the light path in the fundus observation system and the light path in the imaging system.

12. The ophthalmic apparatus according to claim 1, further comprising a display control unit configured to display the image of the anterior segment and the image of the fundus on a display unit.

13. The ophthalmic apparatus according to claim 11, further comprising a display control unit configured to display the image of the anterior segment, the image of the fundus and an image for observing the fundus on a display unit.

* * * * *